(12) United States Patent
Ryan et al.

(10) Patent No.: US 8,549,891 B2
(45) Date of Patent: Oct. 8, 2013

(54) SCRATCH RESISTANCE TEST METHODS AND APPARATUS

(75) Inventors: James Ryan, Powell, OH (US); Alexander Hutter, Plain City, OH (US)

(73) Assignee: Honda Motor Co., Ltd., Tokyo (JP)

( * ) Notice: Subject to any disclaimer, the term of this patent is extended or adjusted under 35 U.S.C. 154(b) by 302 days.

(21) Appl. No.: 12/913,240

(22) Filed: Oct. 27, 2010

(65) Prior Publication Data

US 2012/0103055 A1    May 3, 2012

(51) Int. Cl.
*G01N 3/56* (2006.01)
(52) U.S. Cl.
USPC .................................................. 73/7
(58) Field of Classification Search
USPC .................................................. 73/7
See application file for complete search history.

(56) References Cited

U.S. PATENT DOCUMENTS

| | | | |
|---|---|---|---|
| 2,966,792 A | 1/1961 | Di Pieri | |
| 3,785,198 A | 1/1974 | Heetman | |
| 4,829,839 A | 5/1989 | Fisher et al. | |
| 5,494,707 A | 2/1996 | Wang et al. | |
| 5,804,706 A | 9/1998 | Williston | |
| 6,000,284 A | 12/1999 | Shin et al. | |
| 6,053,052 A | 4/2000 | Starostovic | |
| 6,577,971 B2 | 6/2003 | Aitken et al. | |
| 6,769,287 B2 | 8/2004 | Stewart et al. | |
| 7,272,969 B2 | 9/2007 | Shinohara et al. | |
| 7,302,831 B2 | 12/2007 | Moyse et al. | |
| 2004/0229977 A1 | 11/2004 | Watson et al. | |
| 2008/0000285 A1* | 1/2008 | Gregory et al. | ...................... 73/7 |

* cited by examiner

*Primary Examiner* — Hezron E Williams
*Assistant Examiner* — Paul West
(74) *Attorney, Agent, or Firm* — Capitol City TechLaw, PLLC; Mark E. Duell (57) ABSTRACT

The apparatus and methods disclosed may be utilized for the scratch/mar testing of various materials and components that provide improved correlation between the simulated damage modes and those reasonably expected to be encountered by the final components. The apparatus includes both a fixture configured for receiving and holding the material under test (MUT) and a tool holder that is arranged and configured for supporting and holding a variety of test tools in one or more orientations relative to the MUT. The tool holder and/or the fixture are, in turn, supported by one or more assemblies arranged and configured for bringing the tool into contact with the MUT and providing for movement of the tool relative to the MUT. The apparatus is then used for collecting data from a series of tests that can be used to compare the performance of different MUT compositions and configurations.

11 Claims, 8 Drawing Sheets

SCRATCH RESISTANCE TEST METHODS AND APPARATUS

TECHNICAL FIELD

The present disclosure relates to abrasion and durability test apparatus and test methods for simulating typical use/abuse modes for evaluating the wear and durability characteristics of various types of materials, including, for example, polymeric sheet molding compounds ("SMC"). More particularly, the present disclosure relates to a collection of wear and durability test apparatus and methods that can perform controlled and repeatable abrasion and durability tests during the development of materials and components that will that provide more reliable data during development projects.

BACKGROUND

In light of the increasing use of polymeric materials in vehicle manufacture, surface testing and analysis of such materials and components manufactured from such materials, is a current area of interest in the fields of material science and mechanics. The increased interest in evaluating scratch and/or mar resistance of polymers stems from the increasing use of polymers in various applications including, for example, windshields, appliances, vehicles and other durable goods.

In general, there are two basic types of material surface damage—mar and scratch. The term mar is generally used to refer to those marks caused by a contact with another object that are too shallow to be particularly noticeable under casual observation but nevertheless may become more noticeable when present in large quantities, under close inspection or when highlighted by other conditions. Examples of mar type damage include the damage commonly found on paint coats and dashboard surfaces that have suffered minor damage through contact with small objects such as stones, sticks, car doors or keys that have impacted the surface under evaluation. A scratch is a mark that forms visible grooves and/or surface damage, often referred to as "whitening" of the scratched surface when a lighter substrate is exposed by the removal of or damage to a darker surface layer or coating. A scratch is the more typical damage mode for those surfaces that are subjected to heavier sustained contact with an object that then moves relative to the surface under evaluation. This "whitening" of the scratched surface is a widespread damage mechanism that has prompted much concern in those industries and applications in which the surface condition and/or the residual strength of the damaged article may be a significant factor in a customer's long term satisfaction with the product and/or its residual value.

In order to evaluate the suitability of a composition and/or a particular component, a scratch and/or impact testing device may be applied to a surface or material under test using specified conditions, or a range of specified conditions, to evaluate the ability of the composition or component to resist scratches and/or mars. Analysis of the scratches and/or mars, both during and after the scratch test, may provide useful data and insight into the material properties or surface characteristics of the samples tested in order to guide further development.

Further, a better understanding of the micromechanical properties of materials, derived from surface testing and analysis, and a better understanding of the mechanical process of surface damage may enable quantitative evaluation in the scratch and/or mar behaviors of various materials under a variety of conditions. For example, scratch test data may, and hopefully will, reveal the load conditions under which the material under test begins to sustain and/or accumulate damage to its surface so that the composition and/or design may be adjusted accordingly to improve or maintain the ability of a given material or component to resist or withstand scratch and mar surface damage.

Although a number of conventional surface testing devices and methods have been developed and may provide some useful basis for comparison among various compositions and designs, many focus on relatively small "lab" samples. As a result, these devices and methods tend to utilize testing parameters that do not accurately simulate the damage modes that would be expected during the actual use of the materials and components. For example, some conventional testing methods and apparatus means may yield inconsistent and irreproducible data and results when they are applied to a component under test. For example, for parts that are heavily textured, the small stylus used in some conventional testing devices may be prone to "skip" or "bounce" during testing, thereby contributing to inconsistent testing results. In such instances, the inconsistent and irreproducible data and results complicate the ability of the engineers to produce a valid comparison between competing designs or compositions that would be helpful in guiding further development efforts.

Another concern relates to the range of loads and impact modes that can be applied effectively during scratch testing. In many instances, conventional bench testing is limited in its ability to simulate with a reasonable degree of confidence, the impact and contact conditions that would be reasonably expected to be endured by the materials/components under test during their normal service life. Further, many conventional devices may not allow for variable load or variable scratch speed testing during the completion of a single test. Still further, some conventional scratch testing devices may be unable to measure and capture quantitative data (e.g., load, scratch speed, scratch depth, etc.) during the actual surface test, producing instead a scratched and/or marred sample that is subjected to separate, and generally only qualitative, study. Without gathering quantitative data during testing, it may not be possible to verify that the intended load conditions and scratch speed actually occurred during testing, thereby rendering the test data less useful for comparison and decision making.

One such prior art test method is frequently referred to as the "Ford Five Finger" or "Five Arm" test that corresponds to standards developed for use in the automotive industry that generally corresponds to Ford's BN 108-13 standard, as well as General Motors' GMN3943 standard and Chrysler's LP-463DD-18-01 standard. One apparatus that may be utilized for conducting these tests is the Taber® 710 Multi-Finger Scratch/Mar Tester which includes a pneumatically driven, moveable sledge to which the test sample is mounted. The sledge moves in a linear fashion and allows for single or multiple pass testing and may be operated at various rates of speed relative to the marring tools. An assembly supports five independent splined-fingers that are typically configured to provide a constant, vertical load on interchangeable scratch pins (the scratch pins are typically to provide 1.0 mm or 7.0 mm diameter hemisphere contact surfaces). Individual weights of varying loads may be mounted to the top of each arm finger to exert a standard force on the surface of the test material. Each instrument may be used with a weight set that can include 2N-25N loads.

Although flat specimens up to 22 mm thick are normally tested, the "free-floating" arms enable testing of slightly contoured specimens provided they are rigid or adequately supported. A spring-loaded specimen holder is standard and can be mounted to the end or side of the moveable sledge for greater flexibility. To mount contoured or other non-standard specimens, an optional set of moveable hold-down clamps is available. As will be appreciated, pins having 1.0 mm or 7.0 mm diameter hemispherical contact surfaces, while perhaps delivering repeatable results, do not reflect the sort of damage modes that would be expected to affect polymeric components integrated into vehicles, particularly those incorporated to form exterior surfaces and, in particular, the load-bearing surfaces of pickup cargo beds.

Consequently, there is a need for improved apparatus and methods for surface testing and analysis. In addition, there is a need for surface testing devices and methods which produce reliable and consistent results. Further, there is a need for improved surface testing apparatus and methods that provide the ability to carry out multi-pass, load-controlled scratch tests with variable scratch speed and/or direction. Still further, there is a need for improved surface testing apparatus and methods that measure and capture more realistic damage modes during surface testing.

SUMMARY OF THE DISCLOSURE

The needs identified above and others may be addressed by utilizing the apparatus and methods disclosed infra by which those of ordinary skill in the art can produce repeatable and meaningful scratch and/or mar test data using samples or full-size components. The samples and/or full-size components may be subjected to a range of tests that are selected and configured to provide a reasonable approximation of the various damage modes the components would be expected to suffer in normal or heavy use during a component's expected life cycle.

As will be appreciated, the test procedures can be adapted as necessary to reflect the application for which a particular composition or component is intended. For example, components that make up a load receiving surface could reasonably be expected to suffer more impact and sliding damage than those components that define walls around the load receiving surface. In a first embodiment, the scratch/mar testing device comprises a table or platform on which the material under test may be mounted, a scratching member or tool generally corresponding to a common tool or object, a carriage or other mechanism operable for moving the scratching member relative to the material under test, biasing elements for setting and/or controlling the load that is applied to the scratching member during the test.

Apparatus that may be utilized in the scratch/mar testing according to the disclosure provides a fixture arranged and configured for receiving and holding the material under test (MUT). As will be appreciated, the most basic fixture configuration will simply support and hold the MUT, but other embodiments may provide for linear translation of the MUT along one or more axes, horizontal rotation about a first axis and/or rotation about a second axis that is offset from the first axis and may, for example, be generally perpendicular to the first axis. The apparatus also provides a tool holder that is arranged and configured for supporting and holding a test tool in a desired orientation relative to the MUT. The tool holder is, in turn, supported by an assembly arranged and configured for bringing the tool into contact with the MUT that also allows the tool to be moved relative to the MUT.

As will be appreciated by those skilled in the art, the tool holder(s) may be configured for receiving a wide variety of tools including, for example, shovels, rakes, concrete block and aggregate mixtures, that may be used to simulate the types of damage modes anticipated for the particular MUT.

Similarly, the apparatus may incorporate additional elements such as weights, springs or other biasing means for controlling the force with which the tool is forced against the MUT to provide a reasonable "real-world" simulation. The apparatus may, for example, allow for manual translation of the tool relative to the MUT or, in other embodiments, may incorporate motive elements including, for example, hydraulic, pneumatic, belt-drive or direct-drive systems for initiating and controlling the motion of the tool relative to the MUT.

Utilizing an embodiment of the apparatus, an embodiment of the scratch/mar test method may be completed by securing the material specimen to the fixture, securing and positioning a first tool in the tool holder, applying the tool to the MUT under specified conditions including, for example, force and temperature, and then moving the tool relative to the MUT, again under specified conditions of, for example, velocity, direction, pressure and stroke length and to complete a first test. This basic test sequence would then typically be repeated several more times with other tools, other tool orientation, other tool application and movement protocols and/or other directions relative to the structure of the MUT. Depending on the sample size and the particular tests being performed, multiple tests may be performed on a single MUT, although typically in different regions of the MUT surface or under such other conditions that would allow an evaluator to distinguish a first set of marks from subsequent set(s) of marks. The cumulative data, whether quantitative or qualitative, can then be plotted on a "radar" style chart in which each of the tests has a corresponding axis along which the test data can be plotted for each of the distinct MUTs.

The foregoing summary has outlined some of the features and technical advantages of the apparatus and methods according to embodiments of the present invention in order that the detailed description provided infra may be better understood. Additional features and advantages of the invention will be described in more detail infra and, together with the drawings and the claims help clarify the subject matter defined by the claims. It should be appreciated by those skilled in the art that the conception and the specific embodiments disclosed may be readily utilized as a basis for modifying or designing other structures for carrying out the same purposes of the disclosed invention and that such equivalent constructions and methods are intended to be encompassed in the appended claims.

BRIEF DESCRIPTION OF THE DRAWINGS

The disclosure will be more fully understood from the following detailed description, taken in connection with the accompanying drawings, in which.

It should be noted that these Figures are intended to illustrate the general characteristics of methods, structures and/or materials utilized in certain example embodiments and to supplement the written description provided below. These drawings are not, however, to scale and may not precisely reflect the precise structural or performance characteristics of any given embodiment, and, accordingly, should not be interpreted as defining or limiting the range of values or properties encompassed by example embodiments.

DETAILED DESCRIPTION OF THE DISCLOSURE

As will be appreciated by those in the art, polymeric materials have been incorporated into a wide range of products including, for example, vehicles, as both interior and exterior components. In light of the continued interest in reducing the weight, cost and assembly associated with a particular vehicle, the use of exterior polymeric panels and components that may be manufactured from a variety of materials including, for example, a variety of rigid plastics and extra rigid plastics may be used for external applications that would typically be expected to endure substantial contact events over the life of the part. Examples of such materials include, for example, acrylonitrile butadiene styrene (ABS), polycarbonate (PC), polypropylene (PP), sheet molded compound (SMC), fiberglass reinforced polyester (FRP), polycarbonate/acrylonitrile butadiene styrene (PC/ABS) compositions and Honda polymer alloy (HPA). The materials may be utilized in manufacturing a wide variety of automotive components including, for example, the components that define load carrying enclosures including, for example, the floor and sides of truck beds such as those that can be found in the current Honda Ridgeline®.

As one of the primary justifications for purchasing a pickup truck is its load-carrying capacity, loads such as sand, gravel and mulch that then have to be unloaded from the pickup truck's bed using such common tools as square point shovels, transfer scoops and bow rakes. The materials used in manufacturing the blades used in the shovels and rakes may be made from a variety of materials from the higher end chrome nickel alloy steels to the less expensive carbon steels and, depending on design, use and care, can develop a wide range of blade profiles. When removing material, shovels are generally used with a low angle of attack and a correspondingly low downforce when loading the material onto the shovel blade or with a high angle of attack relative to the surface and a greater downforce with a scraping/gouging motion when scraping the last material out of the bed or driving the shovel into a pile of loose material. Bow rakes, with their large, thick and generally rigid tines, can be used for both leveling and working the soil and are typically moved across the surface downforce sufficient to "bite" into the loose material being applied.

As will be appreciated by those skilled in the art, a variety of tools may be used for simulating other typical damage modes including, for example, movement of concrete block or other masonry supplies, welding tanks, paint cans, buckets, ladders, pipe and other equipment and supplies across a pickup bed during loading/unloading operations and/or during travel when not properly secured. As detailed below, the apparatus may be adapted to accommodate a number of "tools," actual and/or simulated, and range of motion relative to the MUT to simulate a wide variety of damage modes that could reasonably be expected during the anticipated life of the component thereby improving the correlation between test-induced damage and that caused by actual equipment.

With respect to certain of the materials to which the MUT may be exposed, particularly ceramic and concrete based materials, the testing accuracy is dependent on the ability of the applied tool to provide an accurate simulation of the appliance or device it is meant to simulate. One of the characteristics that should be considered is the surface roughness, i.e., a measure of the texture of a surface quantified by the vertical deviations from the ideal planar surface. If these deviations are large, the surface is considered rough while if they are small the surface is considered smooth.

Roughness plays a significant role in determining how an object will interact with its environment. Rough surfaces usually wear more quickly and have higher friction coefficients than smooth surfaces with increased roughness tended to indicate an increased likelihood of failure if the irregularities in the surface serve as nucleation sites for cracks or corrosion on susceptible materials. Roughness may be measured using contact or non-contact methods. Contact methods involve dragging a measurement stylus across the surface; these instruments include profilometers. Non-contact methods of measuring surface roughness include: interferometry; confocal microscopy; focus variation; structured light; electrical capacitance; electron microscopy and photogrametry. For 2D measurements, the probe usually traces along a straight line on a flat surface or in a circular arc around a cylindrical surface. The length of the path traced by the probe is called the measurement length with the wavelength of the lowest frequency filter used to analyze the data typically being defined as the sampling length. Most standards recommend that the measurement length should be 7-10 times greater than the sampling length to provide a reasonable sample.

In the United States, surface finish is usually specified based on the ASME Y14.36M-1996 standard. Other standards that have been employed for evaluating surface finish include both the International Organization for Standardization ISO 1302:2002 and the Australian Standard AS ISO 1302-2005. Depending on the design and manufacturing processes utilized, the surface may exhibit one or more lay patterns including, for example, vertical, horizontal, radial, cross-hatched, circular and isotropic. A lay pattern is a repetitive impression created on the surface of a part or component and is often representative of a specific manufacturing operation. A product designer may also specify a lay pattern on a part because the directionality of the lay affects the part's function. Unless otherwise specified, roughness is typically measured perpendicular to the lay.

A roughness value can either be calculated on a profile or on a surface. The profile roughness parameter ($R_a$, $R_q$, . . . ) are more common. The areal roughness parameters ($S_a$, $S_q$, . . . ) may be more meaningful in some instances. Each of the roughness parameters is calculated using a formula for describing the surface. There are many different roughness parameters in use, but $R_a$ is by far the most common. Other common parameters include $R_z$, $R_q$, and $R_{sk}$. Some parameters are used only in certain industries or within certain countries.

Because these parameters reduce all of the information from a surface profile to a single number, great care should be taken in applying and interpreting them. Relatively small changes in how the raw profile data is filtered, how the mean line is calculated, and the physics of the measurement can greatly affect the calculated parameter. By convention every 2D roughness parameter is a capital R followed by additional subscript characters that identify the particular formula applied to a 2D roughness profile. Different capital letters imply that the formula was applied to a different profile. For example, $R_a$ is the arithmetic average of the roughness profile, $P_a$ is the arithmetic average of the unfiltered raw profile, and $S_a$ is the arithmetic average of the 3D roughness.

In most cases, roughness is considered to be detrimental to part performance. As a consequence, most manufacturing prints establish an upper limit on roughness, but not a lower limit. An exception is in cylinder bores and other lubricated surfaces in which an oil film is retained within the surface profile and require a minimum roughness in order to achieve the desired retention.

Roughness is often closely related to the friction and wear properties of a surface. A surface with a large $R_a$ value, or a positive $R_{sk}$, will usually have high friction and wear quickly. Deep valleys or fissures in the roughness profile are also important in tribology, the branch of engineering that deals with the interaction of surfaces in relative motion, because they may act as lubricant reservoirs. Similarly, the peaks in the roughness profile are not always the points of contact when the macro surface structure is properly considered.

Figure 1:
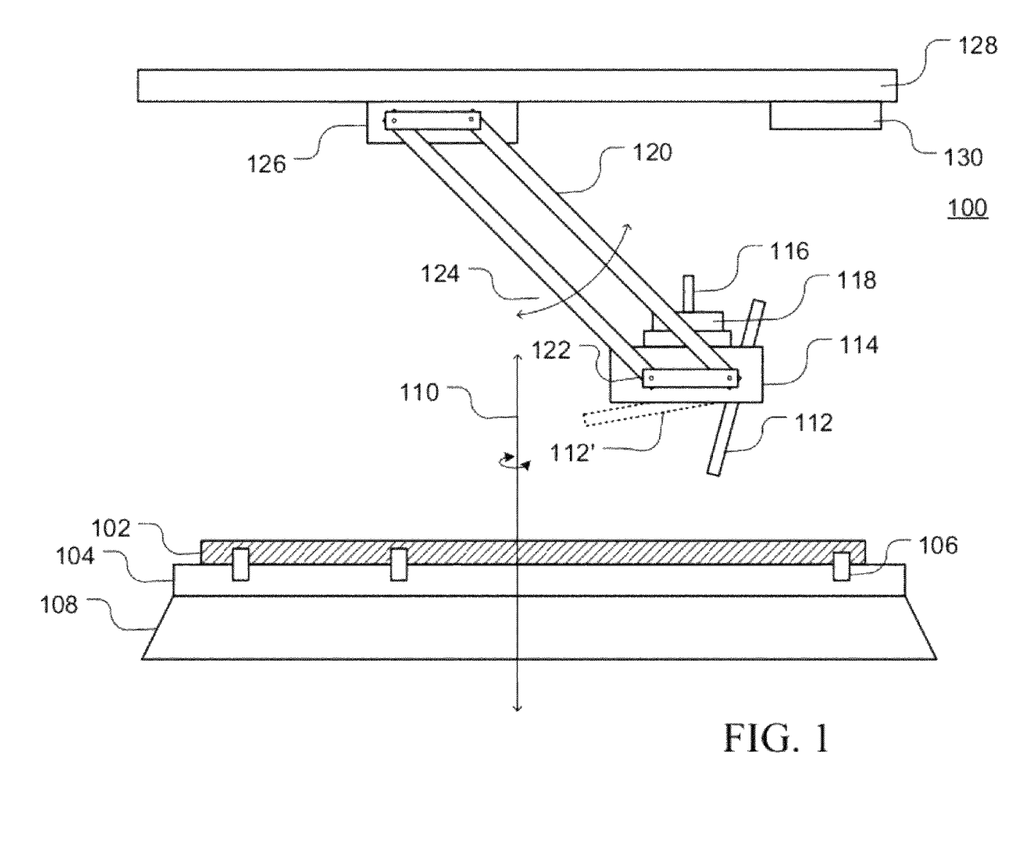
FIG. 1 illustrates an embodiment of an apparatus that may be utilized in conducting scratch/mar testing of various materials and components.

As illustrated in FIG. 1, the apparatus 100 includes a sample of a material under test (MUT) 102, that is supported by and attached to a fixture 104 that, in cooperation with latches, clamps or other preferably releasable holders 106, sets the position of the MUT for the duration of the testing. As indicated in FIG. 1, the fixture may be configured to provide for rotation of the MUT about an axis 110. A tool carrier/ carrier 114 is arranged and configured to support one or more tools 112 in a given orientation and under such conditions as are required for the particular test being conducted.

As also illustrated in FIG. 1, the tool carrier 114 may provide support for a range of tool orientations 112, 112' that will allow a single tool, e.g., a simulated or actual shovel, to be used for simulating both shoveling, low angle of attack, and scraping actions, high angle of attack with a single tool. The tool carrier may be provided with a receiver 116 on to which weight plates 118 may be added to increase the force applied by the tool against the MUT when the tool is engaged. Similarly, springs, hydraulic, pneumatic or other biasing means (not shown) may be utilized for increasing, controlling or decreasing the force of the tool against the MUT. For example, a torsion or tension spring incorporated into the carriage assembly could be used for counterbalancing at least a portion of the tool carrier, tool and associated components.

The tool carrier may be supported on a linkage 120 that allows the tool carrier to be moved into and out of contact with the MUT. As illustrated, the linkage comprises a 4-bar linkage that maintains the tool orientation throughout its range of arcuate movement 124 in order to accommodate various MUT thicknesses without substantial modification of the test apparatus. The opposite end of the linkage may be supported by a carriage 126 that rides along a track 128 in order to provide for linear translation of the tool along the surface of the MUT. The carriage may be moved manually or, optionally, through a motive assembly 130 that may incorporate a screw, belt, pneumatic or hydraulic arrangement in order to move the carriage along the track to provide for unidirectional and/or bidirectional movement of the tool along the surface of the MUT with the tool engaged.

Horizontal and/or rotational movement of the fixture 104 relative to the tool carrier 114, coupled with successive linear motion of the carriage along the track 128 can be used to produce a range of scratch/mar patterns for subsequent analysis. This range of patterns can be particularly useful when the MUT has a non-uniform surface that includes one or more deliberate features including, for example, corrugations, attachment points and/or textured surfaces that may respond differently to tools applied at different angles across the feature. Accordingly, the linear 910, arcuate 912, radial 914 and circular 916 scratch/mar patterns that can be produced by employing various embodiments of the apparatus can be used to test and evaluate the scratch/mar resistance of each of the incorporated features in a single test.

Figure 2:
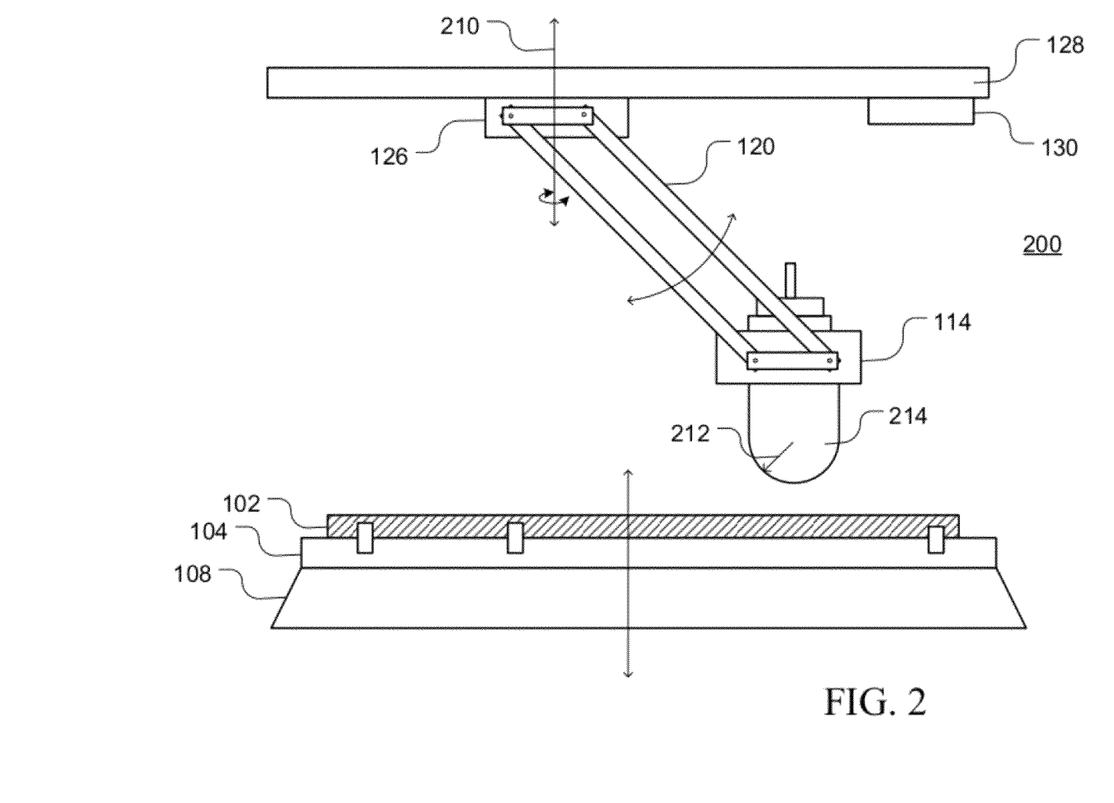
FIG. 2 illustrates another embodiment of an apparatus that may be utilized in conducting scratch/mar testing of various materials and components.

As illustrated in FIG. 2, another embodiment of the apparatus 200 provides for rotation of the carriage about an axis 210 that will permit the movement of a rounded tool 214, characterized by a radius 212, across the surface of the MUT. As will be appreciated, rounded tools of various radii and subjected to various loads can be utilized to simulate various objects that would reasonably be expected to be found in a pickup bed and access the propensity for such objects to damage the particular MUT composition and configuration.

Figure 3:
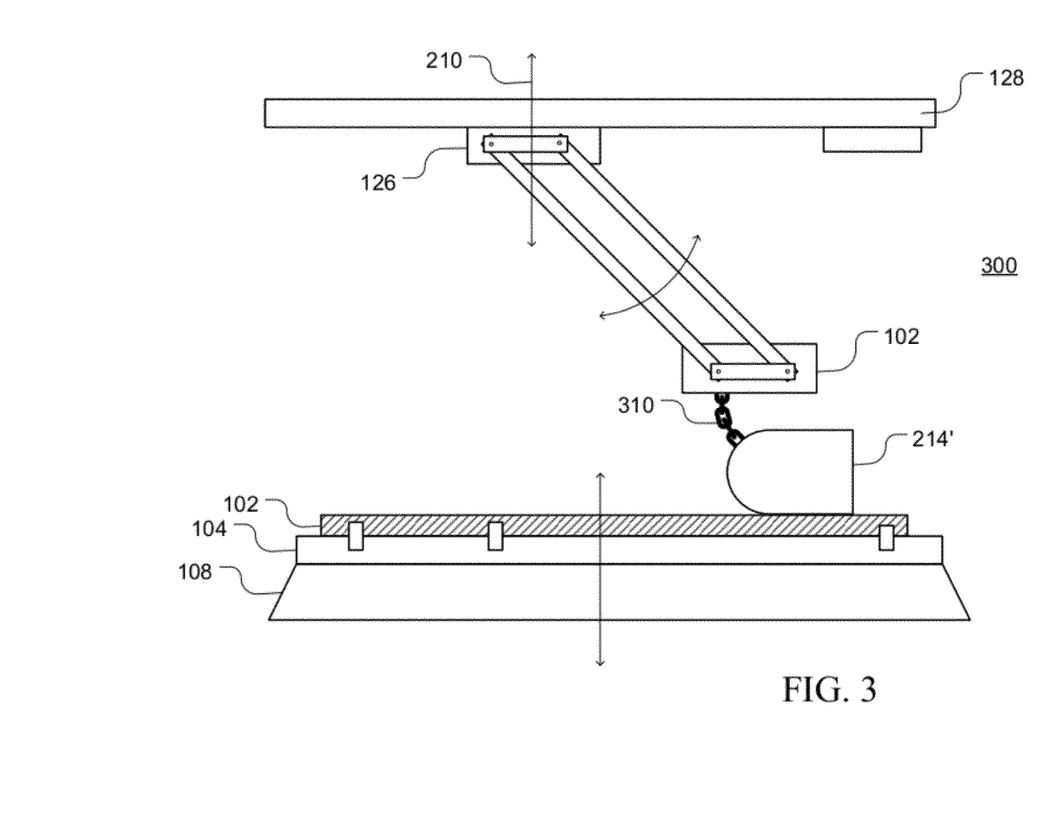
FIG. 3 illustrates another embodiment of an apparatus that may be utilized in conducting scratch/mar testing of various materials and components.

As illustrated in FIG. 3, another embodiment of the apparatus 300 differs from the apparatus as illustrated in FIG. 2 by the means used to attach the tool to the tool carrier. As noted above, one of the anticipated damage modes for pickup beds in normal use is the movement of unrestrained objects across the bed surface. The fixed orientation of the rounded tool as illustrated in FIG. 2, while still useful, may not produce damage sufficiently similar to that of an unrestrained tool. Accordingly, as illustrated in FIG. 3, the tool is attached to the tool carrier in a manner that allows for a range of movement of the tool 214' relative to the tool carrier. Accordingly, chain, cable, swivels and/or other non-rigid restraints 310 are used to allow additional degrees of movement during tool movement. While still not completely "unrestrained," by removing the fixed orientation between the tool and the tool carrier, the illustrated embodiment of the apparatus allows for a more accurate simulation of the damage modes associated with unrestrained objects.

Although illustrated in FIG. 3 with the rounded tool for convenience, it will be appreciated that other tools that more accurately approximate the roughness, structure and hardness of other objects including, for example, masonry and aggregate objects, that would reasonably be expected to be found in a pickup bed. The increased freedom of tool movement provided by this embodiment can be such that the tool is allowed to "tumble" in those instances in which the interaction of surface features provided on the MUT, e.g., corrugation, coupled with movement of the particular tool can lead to interaction between the tool and the surface that tends to rotate the tool with sufficient force.

Figure 4:
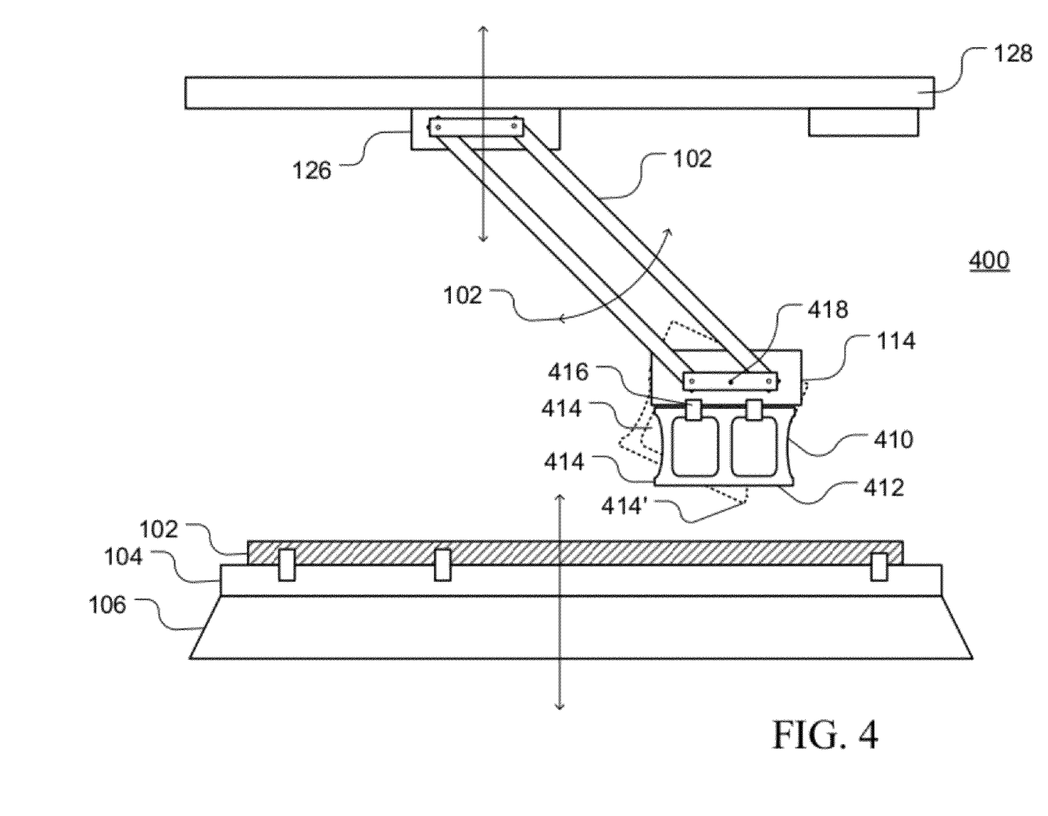
FIG. 4 illustrates another embodiment of an apparatus that may be utilized in conducting scratch/mar testing of various materials and components.

As illustrated in FIG. 4, another embodiment of the apparatus incorporates a tool carrier 114 that, with brackets, latches, straps or other fastening devices 416 can accommodate an increased range of tools including, for example, "cinder" block 410, also sometimes referred to as concrete block, cement block or foundation block. The rough face surface 412 of the block 410 and the edge profile 414 provide various damage modes by which a sliding block could damage a polymeric component such as the MUT 102. Given the degree in variation of surface roughness found in block from various manufacturers, testing consistency could be improved by characterizing the surface roughness, $S_a$ for example, of a sufficient quantity of block to develop roughness ranges that reflect "standard" and/or worse case "rough" block surfaces that could, in turn, be modeled in another hard material that could serve as the tool for subsequent testing. The roughness of the modeled surface could then be periodically evaluated to determine whether it still falls within a designated range of surface roughness or whether it should be replaced.

As noted above, the edge profile 414 of the block 410 can be of concern in addition to the primary surfaces 412 with respect to damage to the MUT. Accordingly, the tool carrier may be arranged and configured to allow for rotation about an axis 418 that would allow the block 410' to be applied against the MUT 102 in an orientation (dashed outline) that accentuates the possibility of damage from the edge profile 414'.

Figure 5:
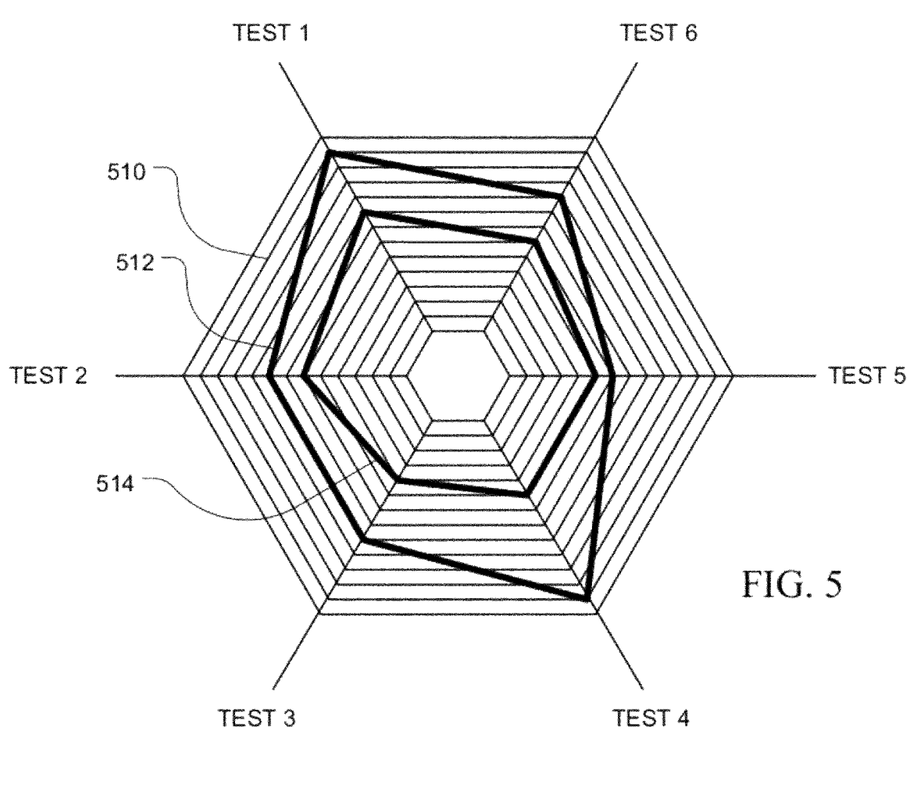
FIG. 5 illustrates an example of how scratch/mar test data generated using various methods and apparatus modifications can be compared with a "radar" plot that reflects the relative performance of the MUTs under a series of test methods.

As illustrated in FIG. 5, the results of a series of scratch/mar tests on different MUT compositions and configurations can be evaluated using a "radar" style plot in which each of the tests corresponds to a radius along which is defined an appropriate scale 510, whether quantitative or qualitative, for evaluating the particular test. Although the embodiment illustrated reflects the results from six distinct tests, the plot may be easily adopted to accommodate different sets of tests. As illustrated in FIG. 5, the results from two different MUTs 512, 514 can be plotted for evaluating the relative performance of the MUTs. As reflected in the plotted data, for example, the first MUT 512 demonstrates significantly better performance than the second MUT 514 in Test 4 while demonstrating very similar performance in Test 5. Depending on the particular nature of the tests, this result may be satisfactory, improvement has been achieved in one area without suffering any corresponding degradation in another area, or may indicate the need for additional work to improve the performance in Test 5.

Figure 7:
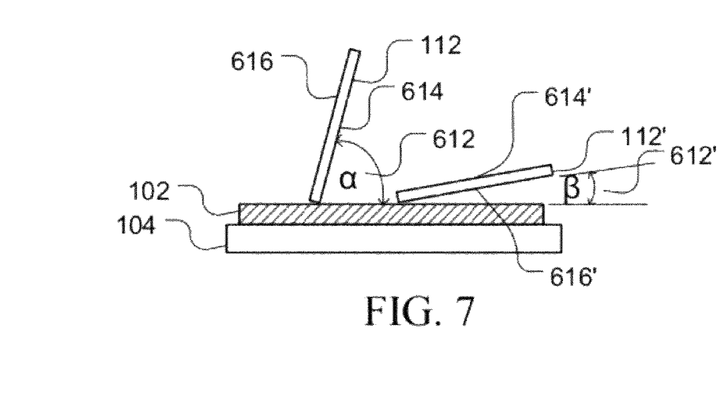
FIG. 7 illustrates various tool orientations relative to the surface of the MUT that may be useful in simulating common uses to which a particular MUT would likely be subjected.

As illustrated in FIG. 7, which provides additional detail regarding an embodiment of the apparatus as illustrated in FIG. 1, the tool holder may be arranged and configured to provide various angles of attack between a tool, such as a tool simulating a shovel blade, and the MUT 102. As illustrated in FIG. 7, a shovel gouge damage mode can be simulated by arranging the tool 112 at a relatively high angle of attack a relative to the surface of the MUT in order to simulate clearing a relatively thin layer of material from a pickup bed. Alternatively, the tool 112' can be arranged at a relatively low angle of attack β to better simulate the damage mode that would correspond to shoveling material from the pickup bed.

To the extent that the tool has a non-linear edge profile in which the faces 614, 616 are different, the orientation of the tool can be modified to better simulate the effects of a shovel or rake being moved across the MUT. Accordingly, the orientation of the tool would typically be reversed between the scraping mode, 614, 616 and the shoveling mode 614', 616' to provide a more authentic test of the MUT's ability to resist damage.

Figure 8:
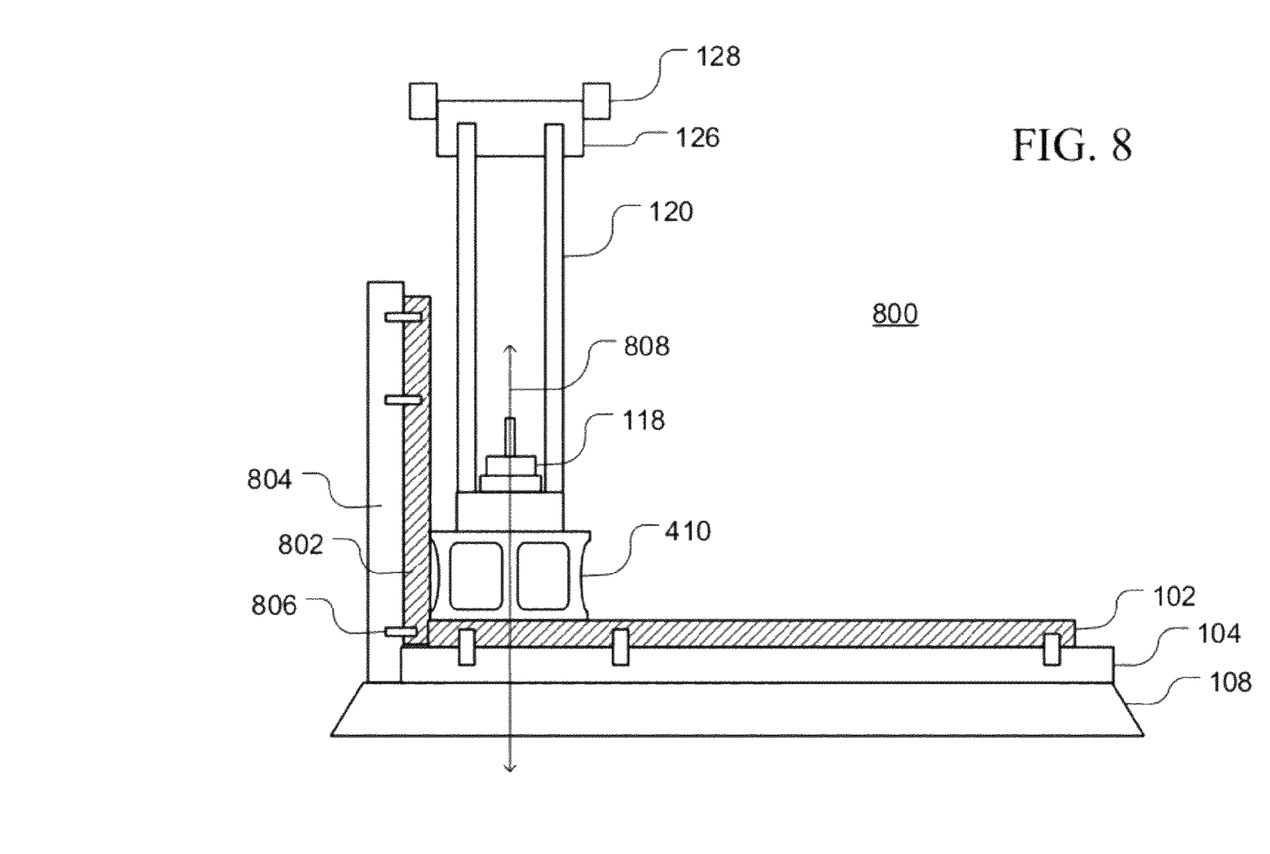
FIG. 8 illustrates another embodiment of an apparatus that may be utilized in conducting scratch/mar testing of various materials and components.
Figure 9A:
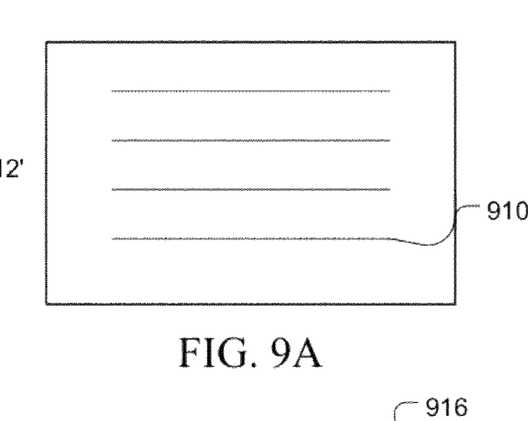
FIGS. 9A-9C illustrate various scratch/mar patterns that can be induced on the material under test utilizing one or more of the embodiments of the apparatus detailed below.
Figure 9B:
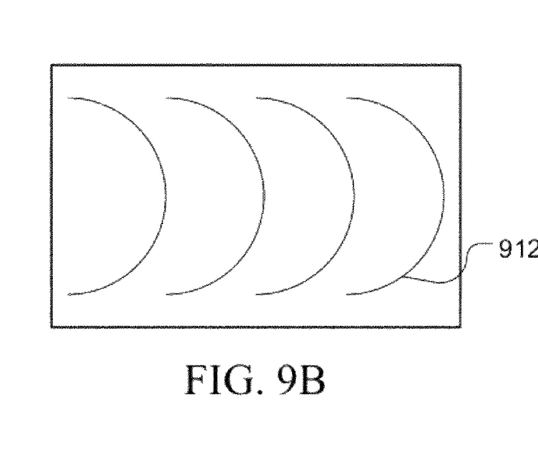
Figure 9C:
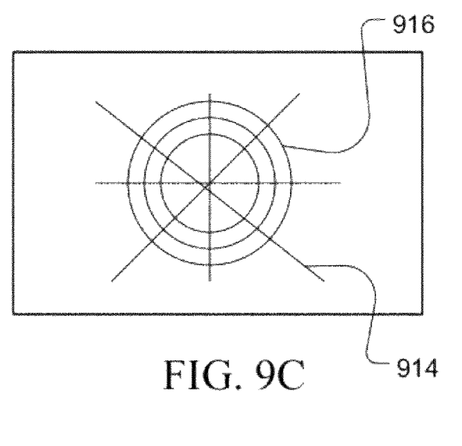

As illustrated in FIG. 8, because the nature of the contact between an object and a surface is highly orientation dependent, another embodiment of the apparatus 800 provides for the simultaneous testing of both horizontally and vertically arranged MUTs corresponding, for example, to the bed and sidewalls of a pickup bed. As illustrated in FIG. 8, a second fixture 804 and appropriate attachments 806 are utilized for arranging a second MUT 802 in a generally perpendicular orientation relative to the first MUT 102. By appropriately positioning the fixtures and the carriage 126, the tool 410 can be brought to bear against both horizontal and vertical surfaces. Again, as noted about, the non-uniform configuration of particular tools and the corresponding impact on the relevant damage modes can be further evaluated by providing for rotation of the tool about an axis 808 projecting through the tool holder in order to bring different surfaces of the tool into contact with the second MUT surface. Springs or other biasing means (not shown) may be used to maintain substantially constant pressure between the contact surface of the tool and the surface of the second MUT.

Utilizing an embodiment of the apparatus as described above, a variety of tests can be performed to simulate damage modes that would be expected for various automotive components. For example, a sequence of abrasion tests may include, for example:

Cinder Block Test
1. Position the tool (cinder block or simulated surface) so that its primary surface rests on the surface of the material under test; the material under test being maintained at 20-30° C.
2. Move the tool across the surface in a linear fashion, completing a specified number of passes, for example, 10, with a substantially constant load applied.
3. Remove the tool and evaluate the surface of the material under test.

Shovel Gouge Test
1. Position the tool (shovel or simulated tool) so that its leading edge is oriented at an intermediate angle (~45°) relative to the surface of the material under test; the material under test being maintained at 20-30° C.
2. Bring the tool into contact with the surface with a substantially constant force, completing a specified number of contacts, for example, 5.
3. Remove the tool and evaluate the surface of the material under test.

Shovel Scrape Test
1. Position the tool (shovel or simulated tool) so that its leading edge is oriented at a shallow angle (~20°) relative to the surface of the material under test; the material under test being maintained at 20-30° C.
2. Bring the tool into contact with the surface with a substantially constant force, completing a specified number of contacts, for example, 5.
3. Remove the tool and evaluate the surface of the material under test.

Shovel Drag Test
1. Position the tool (shovel or simulated tool) so that its leading edge is oriented at a high angle (~75°) relative and is in contact with the surface of the material under test; the material under test being maintained at 20-30° C.
2. Move the tool across the surface in a linear fashion, completing a specified number of passes, for example, 5, with a substantially constant load applied.
3. Remove the tool and evaluate the surface of the material under test.

Rounded Object Test
1. Position the tool (tank or simulated tool) so that its rounded surface is in contact with the surface of the material under test; the material under test being maintained at 20-30° C.
2. Move the tool across the surface in a linear fashion, completing a specified number of passes, for example, 10, with a substantially constant load applied.
3. Remove the tool and evaluate the surface of the material under test.

Rake Test
1. Position the tool (rake or simulated tool) so that its tines or other projections are in contact with the surface of the material under test at a relatively shallow angle; the material under test being maintained at 20-30° C.

2. Move the tool across the surface in a linear fashion, completing a specified number of passes, for example, 20, with a substantially constant load applied.

3. Remove the tool and evaluate the surface of the material under test.

As will be appreciated, these basic tests can be modified in a number of ways to simulate extended wear (increasing the number of passes); severe wear (by increasing the applied load/force and/or applied angle); evaluate surface features (by changing the direction and/or path of the tool movement relative to the features of interest); evaluate environmental issues (by increasing or decreasing material temperature) and/or simply better simulate a reported failure/damage mode from the field. As will also be appreciated, the orientation of the material under test may be modified relative to the tool to simulate more accurately the mode of contact that would be expected between the applied tool and the surface. Accordingly, bed and sidewall components can be arranged to reflect their substantially perpendicular orientation while under test.

Figure 6A:
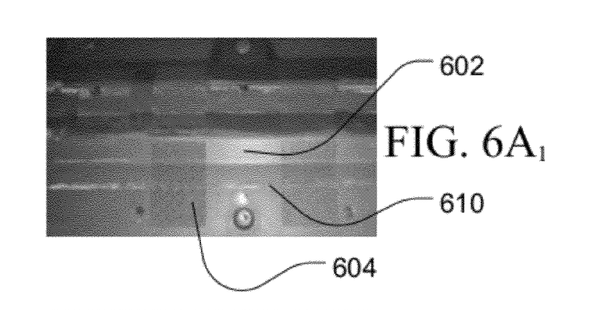
FIGS. 6A and 6B illustrate examples various MUT compositions after being subjected to a series of scratch/mar tests.
Figure 6A:
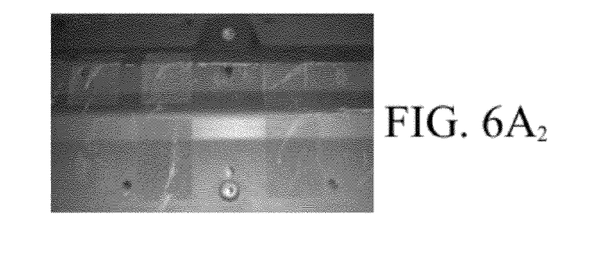
Figure 6A:
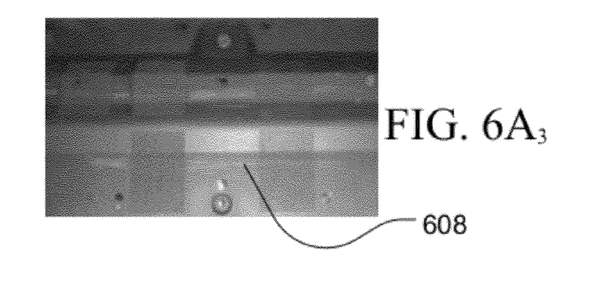

As illustrated in FIGS. $6A_1$ to $6A_3$, samples of a non-UV stable SMC having both "smooth" 602 and "textured" 604 regions distributed across the surface were subjected to cinder block, FIG. $6A_1$, shovel gouge, FIG. $6A_2$, and rounded tool drag, FIG. $6A_3$, testing, resulting in various degrees of surface damage 608, 610.

Figure 6B:
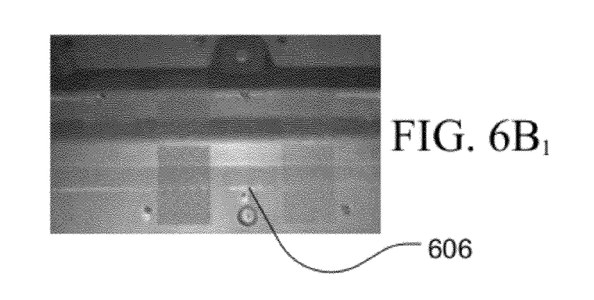
Figure 6B:
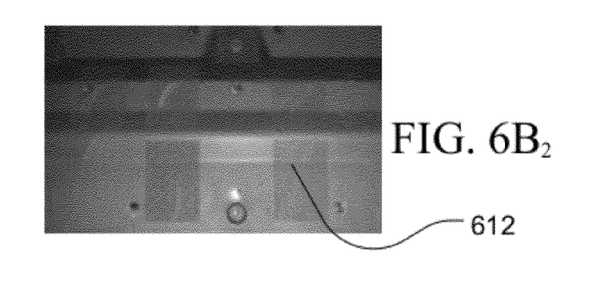
Figure 6B:
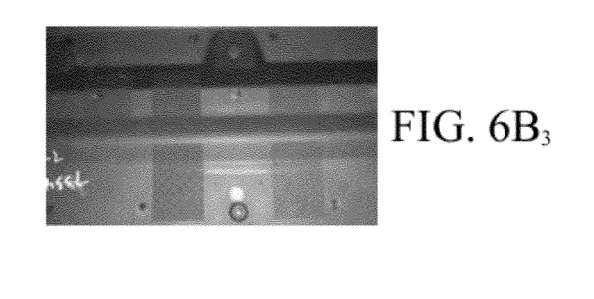

As illustrated in FIGS. $6B_1$ to $6B_3$, samples of a UV stable SMC having both "smooth" and "textured" regions distributed across the surface were subjected to cinder block, FIG. $6B_1$, shovel gouge, FIG. $6B_2$, and rounded tool drag, FIG. $6B_3$, testing, resulting in various degrees of surface damage 606.

While the present disclosure as included descriptions of various embodiments, it should be understood that these embodiments are not intended to limit the disclosure and that one of skill in the art, guided by the present disclosure, can adopt the methods and apparatus disclosed to test other wear/damage modes associated with other tools and/or actions. Accordingly, the present disclosure is intended to encompass such alternatives, modifications, and equivalents as may be included within the spirit and scope of the appended claims.

We claim:

1. A method of evaluating the durability of cooperating surfaces comprising:
   positioning a first test sample on a first fixture to expose a first test surface;
   positioning a second test sample on a second fixture to expose a second test surface, the first and second test surfaces defining an offset angle;
   bringing a first surface of a tool into contact with the first test surface;
   bringing a second surface of the tool into contact with the second test surface;
   moving the tool in a manner whereby the first surface of the tool moves across the first test surface in a first direction while a first test load is applied and the second surface of the tool moves across the second test surface in a second direction while a second test load is applied;
   removing the test samples from the fixture; and evaluating the test surfaces.

2. The method of evaluating the durability of cooperating surfaces according to claim 1, wherein:
   the offset angle is 90°.

3. The method of evaluating the durability of cooperating surfaces according to claim 1, wherein:
   the first test load, TL1, is greater than the second test load, TL2.

4. The method of evaluating the durability of cooperating surfaces according to claim 3, wherein:
   the ratio of the first test load to the second test load, TL1:TL2, is at least 4:1.

5. An apparatus comprising:
   a base fixture arranged and configured for holding a first test sample;
   a second fixture arranged and configured for holding a second test sample,
   a tool carrier arranged and configured for receiving a test tool;
   an assembly arranged and configured for bringing a wear surface of the test tool into contact with an exposed surface of the first test sample; and
   a carriage arranged and configured to support the assembly and to provide for movement of the test tool relative to both the first and second test samples,
   wherein an offset angle is defined between an exposed surface of the second test sample and the base fixture.

6. The apparatus according to claim 5, wherein:
   the base fixture is arranged and configured to allow for linear and rotational movement relative to the tool carrier.

7. The apparatus according to claim 5, wherein:
   the assembly further comprises biasing means for modifying the forces with which the test tool contacts the exposed surfaces of the first and second test samples, respectively.

8. The apparatus according to claim 5, wherein:
   the assembly further comprises an axis that allows for rotational movement of the tool carrier relative to the exposed surface of the second test sample.

9. The apparatus according to claim 5, wherein:
   the tool carrier further comprises a pivot that allows for arcuate movement of the tool carrier across the exposed surface of the second test sample.

10. The apparatus according to claim 5, wherein:
    the offset angle is 90°.

11. The apparatus according to claim 5, wherein:
    the wear surface of the test tool in contact with the exposed surface of the test sample is not fixed.

* * * * *